US007053203B1

(12) United States Patent
Hirochika et al.

(10) Patent No.: US 7,053,203 B1
(45) Date of Patent: May 30, 2006

(54) GENE CONTROLLING ETHYLENE SYNTHESIS

(75) Inventors: Hirohiko Hirochika, Ibaraki (JP); Kiyomi Abe, Saitama (JP)

(73) Assignees: Natl. Institute of Agrobiological Sciences, Ibaraki (JP); Bio-Oriented Technology Research Advancement Institution, Saitama (JP)

( * ) Notice: Subject to any disclaimer, the term of this patent is extended or adjusted under 35 U.S.C. 154(b) by 0 days.

(21) Appl. No.: 09/979,432

(22) PCT Filed: May 25, 1999

(86) PCT No.: PCT/JP99/02732

§ 371 (c)(1), (2), (4) Date: Mar. 5, 2002

(87) PCT Pub. No.: WO00/71721

PCT Pub. Date: Nov. 30, 2000

(51) Int. Cl.

| | |
|---|---|
| ***C12N 15/29*** | (2006.01) |
| ***C12N 15/82*** | (2006.01) |
| ***A01H 5/00*** | (2006.01) |
| ***A01H 5/06*** | (2006.01) |

(52) U.S. Cl. ................. 536/23.6; 536/23.1; 435/320.1; 800/278; 800/283; 800/298; 800/300; 800/320.2

(58) Field of Classification Search ............... 536/23.1, 536/23.2, 23.6; 800/278, 283, 290, 298, 800/320.2; 435/320.1

See application file for complete search history.

(56) References Cited

U.S. PATENT DOCUMENTS 5,723,766 A * 3/1998 Theologis et al. .......... 800/283

OTHER PUBLICATIONS

Zarembinski T. et al. Molecular Biology of the Cell, Apr. 1993; vol. 4, pp. 363-373.*

Adams-Phillips L. et al. Plant Molecular Biology, 2004, vol. 54; pp. 387-404.*

Shen et al. J. of Biol. Chem. May 15, 1991, vol. 266, No. 14, pp. 8963-5968.*

Broun P. et al. Science vol. 282; Nov. 13, 1998, pp. 1315-1317.*

Akama et al. 1992, Plant Cell Reports; vol. 12, pp. 7-11.*

* cited by examiner

*Primary Examiner*—Russell P. Kallis
(74) *Attorney, Agent, or Firm*—Perkins Coie LLP

(57) ABSTRACT

An oligonucleotide encoding a plant gene capable of controlling ethylene synthesis, comprising an oligonucleotide encoding an amino acid sequence from position 1 (Met) to 405 (Gln) of SEQ ID NO. 2 in SEQUENCE LISTING, or an oligonucleotide encoding a second amino acid sequence having one or several amino acid deletions, substitutions, or additions in the amino acid sequence.

5 Claims, 5 Drawing Sheets

FIG. 1

```
                                                                                ▽Intron1(~340)
GCGTAAGAAA AATAAAAGGA GAAAAAGGAA TAGAGAAATT GGGGAAGAGA GCTACCTCGA ATCGAAGCTG CGATCTCCAC CTGGTGAAAT AGGAGAATTG ATGAATTGCT GAGATTTGGT  120
                          ▽Intron2(~615)
GATTAGAGGG ACCTTTGCTG CTGAGGCATT GAGGTACACT AAAAGCAAGG GTGTGAAAAA GGCAACTTCA ATTGAAAACA TCTACATATC TAGGAATGTC CTGAAACTAA TGTGTGGAGT  240

AAACTTCTAG TTTATTGCTG TCCGTCCTGT TGGGCCACAG TGCGAAGGTC AGGCAGTAGT CATCCATTAC TGATGGGGGA CTCTGGAAAT GCCAGTCATC GTGATCACAC GATCGACATA  360
                                                                              M  G  D   S  G  N   A  S  N   R  D  H   T  I  D  I   16

CTGAGAAATG ATGCAACTTT CCCATCAACA TCTCATCAGG ATAATCATAA TAACTTGGAT GAGTTGCACC AAACTAGAGG GCCTCTAAAT GATGTTCCTC ATGTCCCAGA AAGTTCTGCT  480
 L  R  N   D  A  T  F   P  S  T   S  H  Q   D  N  H  N   N  L  D   E  L  H   Q  T  R  G   P  L  N   D  V  P   H  V  P  E   S  S  A   56

AGTGCAACTC CTGCATCTAT CTCCCGAAAC GCTTCTTTTG CAAGAAGAGA TCAAGAACAC CGTCAACCAA ATCCTTTGAA TTCTGGCTTC TGGATCTCAA TTGAGCTTAT TGTAAGTTTA  600
 S  A  T   P  A  S  I   S  R  N   A  S  F   A  R  R  D   Q  E  H   R  Q  P   N  P  L  N   S  G  F   W  I  S   I  E  L  I   V  S  L   96

AGCCAGATTA TAGCAGCTAT TACTGTCCTG TCAGTATCAA GGAACGAGCA TCCTCATGCT CCTTTGGCTC AGTGGCTTAT TGGTTATACG ATAGGTTGTG TTGCTACTCT TCCTCACCTT  720
 S  Q  I   I  A  A  I   T  V  L   S  V  S   R  N  E  H   P  H  A   P  L  A   Q  W  L  I   G  Y  T   I  G  C   V  A  T  L   P  H  L  136

TATTGGCGAT TTCTCCACCG CAATCGGCAG AACACAGAGC AAGAATCAAC AAATCAGGTT TCATCTGAAA GGGACGTATA TGAGCCTAAT TCTTATGTAG TAGTTTCGTC TGCTCATGGA  840
 Y  W  R   F  L  H  R   N  R  Q   N  T  E   Q  E  S  T   N  Q  V   S  S  E   R  D  V  Y   E  P  N   S  Y  V   V  V  S  S   A  H  G  176

                                        ⇩Tos17 insertion
                                        ▽Intron3(~365)
TCAGAAGTTG TGGACAGTGG TAATAATGGT GGAGTAGCAA GGATTGCAAG TCCAAGGGTC TACGCATTGG TTGCGTGCTT CAAATTGGCT CTGGATTGTT TCTTTGCTGT GTGGTTTGTT  960
 S  E  V   V  D  S  G   N  N  G   G  V  A   R  I  A  S   P  R  V   Y  A  L   V  A  C  F   K  L  A   L  D  C   F  F  A  V   W  F  V  216
                                                ▽Intron4(~85)
GTTGGGAATG TGTGGATATT CGGGGGGCGT ACTTCTCTCC ATGACGCTCC TAACTTGTAC AGGCTGTGCA TAGTATTCCT TGCATTCGGC TTCATCGGCT ATGCCCTGCC TTTCATCCTA 1080
 V  G  N   V  W  I  F   G  G  R   T  S  L   H  D  A  P   N  L  Y   R  L  C   I  V  F  L   A  F  G   F  I  G   Y  A  L  P   F  I  L  256

TGTACAATGA TATGCTGCTG CCTACCCTGC ATTATCTCCA TGATGGGCAT CCACGAGGAT TTGGATTTTA ACAGAGGCGC TACTGCAGAA GCAATCGATG CCTTGGTGGC ATACAAGTTC 1200
 C  T  M   I  C  C  C   L  P  C   I  I  S   M  M  G  I   H  E  D   L  D  F   N  R  G  A   T  A  E   A  I  D   A  L  V  A   Y  K  F  296
                                                                                                          ▽Intron5(~127)
CAATCGAAAA AGTTTCAAGA TGGAGAAGCG GGAGAAGATA ATGGTGGAGT ATTGGCAGCT GGAACAGACA AAGAGCGAAC TATTTCTGCA GAAGACGCTG TATGCTGCAT CTGCTTGTCA 1320
 Q  S  K   K  F  Q  D   G  E  A   G  E  D   N  G  G  V   L  A  A   G  T  D   K  E  R  T   I  S  A   E  D  A   V (C) C  I (C)  L  S  336

AAGTTCTCAA ACAACGAAGA TCTACGGGAG CTTCCCTGCA ATCATGTTTT CCACTTGGAA TGCGTCGATA AATGGCTCAA GATAAACGCA CTGTGCCCTC TTTGCAAGGC TGACTTAGGC 1440
 K  F  S   N  N  E  D   L  R  E   L  P (C)  N (H) V   F (H) L   E (C) V   D  K  W  L   K  I  N   A  L (C)  P  L (C)  K  A   D  L  G  376

GGCTCGACGA ATGCTCCGGA CTCGAGCTCC AGGAGCAGCC ATGACAGCAA CAACAGCAGA GTCAGGAACG ACGTCGAGTC ACAACAGTAG CTGCTCTCAT GCCCTTTCCC ATGAGCATGG 1560
 G  S  T   N  A  P  D   S  S  S   R  S  S   H  D  S  N   N  S  R   V  R  N   D  V  E  S   Q  Q                                       405

GGATGGAACA CATTCTTGAC AATCTACAAA TTGGCATGCA ACTTCTCAAG TCCCTTTTTT TTTCAGACAG ACTTGAATAG AGCATTTGCC TACACTGCTC TCTGGTGTTA ACCCAGAAAC 1680

TCCTATGAGG CTGAGGCTAT GGCTATGAGT TGCTGCCTGC AGTTTGTTCT GAACTGAAGT TGCCTGTAAG GCTGTAACAG ATTATAGATG GTGTTGGAAT AGTTATCATG ATGATCACCT 1800

GAGTTGAGCA TATTAGGTTG TTGAGGTTAA CCTTCAACCG GGGAGGTTCA ATGTAATTAT CTCCTTGTTT AGGAAAAAAT CCCCTCCCCT TTGTATTTGC TCCCTTGTAT AGAAAACAAC 1920

CATTTCCATT GTATATCAGA TCAATTTTGC CTGCATTTTG TAAATTCAGT TAGTAGGCAG AGATTTCCCA GCAATCATCA AGCGGTTGAG CAAGTACAGA TTAGCAGTTG AGTTTATTTT 2040

ACTGTAATGC AACAATTATA GATGATATTA CCATGAAATA ATCATTTGAG CCCAAAAAAA AAAAA                                                            2105
```

GENE CONTROLLING ETHYLENE SYNTHESIS

This application claims priority to application no. PCT/JP99/02732 filed 25 May 1999, now publication no. WO 00/71721 published 30 Nov. 2000 which is incorporated herein by reference.

TECHNICAL FIELD

The present invention relates to a novel gene. More particularly, the present invention relates to a novel gene encoding a protein having a function of controlling ethylene synthesis in a plant.

BACKGROUND ART

Transposons are mutagenic genes which are ubiquitous in the genomes of animals, yeast, bacteria, and plants. Transposons are classified into two categories according to their transposition mechanism. Transposons of class II undergo transposition in the form of DNA without EYED replication. Examples of class II transposons include Ac/Ds, Spm/dSpm and Mu elements of maize (*Zea mays*) (Fedoroff, 1989, Cell 56, 181–191; Fedoroff et al., 1983, Cell 35, 235–242; Schiefelbein et al., 1985, Proc. Natl. Acad. Sci. USA 82, 4783–4787), and Tam element of Antirrhinum (Antirrhinum majus) (Bonas et al., 1984, EMBO J, 3, 1015–1019). Class II transposons are widely used in gene isolation by means of transposon tagging. Such a technique utilizes a property of transposons. That is, a transposon transposes within a genome and enters a certain gene and, as a result, such a gene is functionally modified, whereby the phenotype controlled by the gene is changed. If such a phenotype change can be detected, the affected gene may be isolated (Bancroft et al., 1993, The Plant Cell, 5, 631–638; Colasanti et al., 1998, Cell, 93, 593–603; Gray et al., 1997, Cell, 89, 25–31: Keddie et al., 1998, The Plant Cell, 10, 877–887; Whitham et al., 1994, Cell, 78, 1101–1115).

Transposons of class I are also called retrotransposons. Retrotransposons undergo replicative transposition through RNA as an intermediate. A class I transposon was originally identified and characterized in *Drosophila* and yeast. A recent study has revealed that retrotransposons are ubiquitous and dominant in plant genomes (Bennetzen, 1996, Trends Microbiolo., 4, 347–353; Voytas, 1996, Science, 274, 737–738). It appears that most retrotransposons are an integratable but non-transposable unit. Recently, it has been reported that some retrotransposons of such a type are activated under stress conditions, such as injury, pathogen attack, and cell culture (Grandbastien, 1998, Trends in Plant Science, 3, 181–187; Wessler, 1996, Curr. Biol., 6, 959–961; Wessler et al., 1995, Curr. Opin. Genet. Devel., 5, 814–821). For example, such activation under stress conditions was found in retrotransposons of tobacco, Tnt1A and Tto1 (Pouteau et al., 1994, Plant J., 5, 535–542; Takeda et al., 1988, Plant Mol. Biol., 36, 365–376), and a retrotransposon of rice, Tos17 (Hirochika et al., 1996, Proc. Natl. Acad. Sci. USA, 93, 7783–7788).

The rice retrotransposon Tos17 is a class I element in a plant which has been extensively studied. Tos17 was cloned by RT-PCR using degenerate primers which had been prepared based on a conserved amino acid sequence of the reverse transcriptase domains of Ty1-copia group retroelements (Hirochika et al., 1992, Mol. Gen. Genet., 233, 209–216). Tos17 has a length of 4.3 kb and has two identical LTRs (long terminal repeats) of 138 bp and a PBS (primer binding site) which is complementary to the 3' end of the initiator methionine tRNA (Hirochika et al., 1996, supra). Transcription of Tos17 is strongly activated by tissue culture, and the copy number of Tos17 increases with time in culture. Its initial copy number in Nipponbare, which is a japonica variety as a genome research model, is two. In plants regenerated from tissue culture, its copy number is increased to 5 to 30 (Hirochika et al., 1996, supra). Unlike class II transposons found in yeast and *Drosophila*, Tos17 undergoes random transposition in a chromosome and induces mutation in a stable manner. Therefore, Tos17 provides a useful tool in reverse genetics for analyzing the function of a gene in rice (Hirochika, 1997, Plant Mol. Biol. 35, 231–240: 1999, Molecular Biology of Rice, K. Shimamoto Ed., Springer-Verlag, 43–58).

DISCLOSURE OF THE INVENTION

The present invention provides a novel plant gene provided using Tos17.

The inventors have diligently studied and systematically analyzed the phenotypes of plants having a newly transposed Tos17 copy and sequences flanking a Tos17 target site. As a result, the inventors obtained a rice mutant having inhibited growth of lateral roots due to Tos17 insertion and examined the Tos17 target site to find a novel gene capable of controlling ethylene synthesis, thereby completing the present invention.

The present invention relates to an oligonucleotide encoding a plant gene capable of controlling ethylene synthesis, comprising an oligonucleotide encoding an amino acid sequence from position 1 (Met) to 405 (Gln) of SEQ ID NO. 2 in SEQUENCE LISTING, or an oligonucleotide encoding a second amino acid sequence having one or several amino acid deletions, substitutions, or additions in the amino acid sequence.

Preferably, the oligonucleotide is derived from rice.

Preferably, the oligonucleotide is represented by SEQ ID NO. 1 in SEQUENCE LISTING.

In one aspect, the present invention relates to a vector comprising the above-described oligonucleotide operatively linked to a control sequence.

Preferably, the vector is pIG121-Hm-RF.

In another aspect, the present invention relates to a plant including the above-described oligonucleotide and a plant transformed with the above-described vector.

Further, the present invention relates to a method for controlling ethylene synthesis, comprising the step of introducing the above-described oligonucleotide into a plant.

BRIEF DESCRIPTION OF THE DRAWINGS

FIG. 1 is a diagram showing the nucleotide sequence (SEQ ID NO:1) and encoded amino acid (SEQ ID NO:2) of an oligonucleotide according to the present invention. In the figure, triangle marks indicate the positions of introns. The numbers inside parentheses indicates the number of nucleotides in the intron. The downward arrow above the third intron in the middle of the figure indicates the position of Tos17 insertion. Four downward arrows shown in the lower portion of the figure indicate polyadenylation sites. Underlined portions indicate hydrophobic residue rich regions. Encircled amino acid residues indicate $Zn^{2+}$-bound residues conserved in a RING finger region.

BEST MODE FOR CARRYING OUT THE INVENTION

Figure 2:
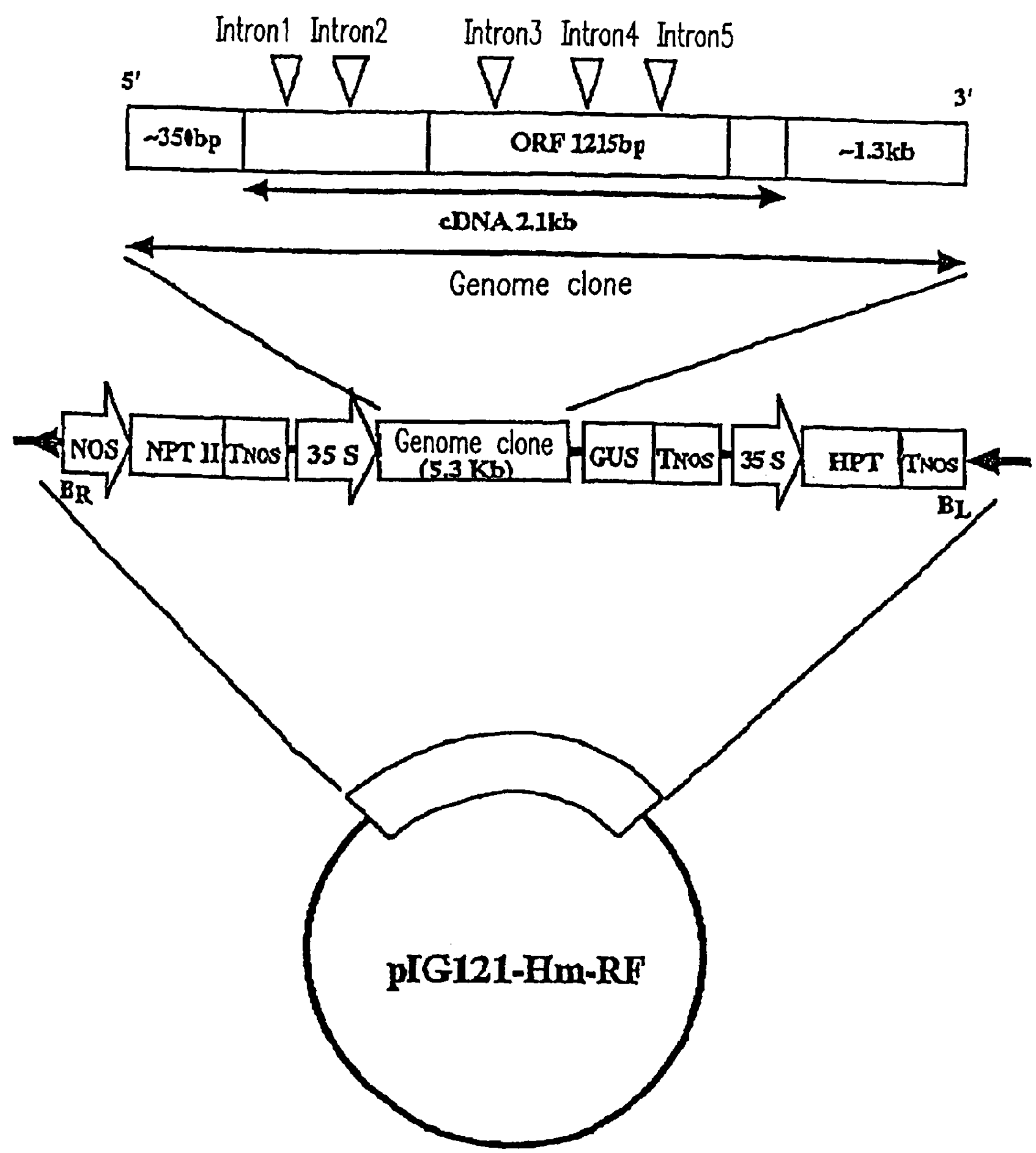
FIG. 2 is a diagram showing construction of a complementary vector in a complementation test.

The present invention provides a novel plant gene provided using Tos17, a vector including the novel gene, a plant transformed with the novel gene, and a method for improving a plant comprising the step of transforming a plant with the novel gene.

The present invention provides an oligonucleotide encoding a plant gene capable of controlling ethylene synthesis. The term “capable of controlling ethylene synthesis” as used herein refers to suppression or activation of expression of a gene involved in ethylene biosynthesis in a plant. The term “plant” refers to both monocotyledons and dicotyledons.

Representative examples of an oligonucleotide according to the present invention, which encodes a plant gene capable of controlling ethylene synthesis, include an oligonucleotide comprising an oligonucleotide encoding an amino acid sequence from position 1 (Met) to 405 (Gln) of SEQ ID NO. 2 in SEQUENCE LISTING, or an oligonucleotide encoding an amino acid sequence having one or several amino acid deletions, substitutions, or additions in that amino acid sequence.

The oligonucleotide of the present invention, which encodes a plant gene capable of controlling ethylene synthesis comprises an oligonucleotide having at least an 80% sequence identity with an amino acid sequence from position 303 (Asp) to 376 (Gly) of SEQ ID NO. 2 in SEQUENCE LISTING, preferably at least an 85% sequence identity, more preferably at least a 90% sequence identity, even more preferably at least a 95% sequence identity, and most preferably at least a 99% sequence identity, as long as the oligonucleotide is capable of controlling ethylene synthesis in a plant. The term “sequence identity” refers to that two oligonucleotides of interest have the same sequence. The percentage (%) of sequence identity between two oligonucleotide sequences of interest is calculated as follows: the two oligonucleotide sequences are optimally aligned: sequence positions having the same nucleic acid base (e.g., A, T, C, G, U, or I) between the sequences are counted and the total number of matching positions is called the matching position number; and the matching position number is divided by the total number of bases of the two oligonucleotides and the result is multiplied by 100. The sequence identity may be, for example, calculated using the following sequence analyzing tools: Unix-based GCG Wisconsin Package (Program Manual for the Wisconsin Package, Version 8, September 1994, Genetics Computer Group, 575 Science Drive Madison, Wis., USA53711; Rice, P., (1996) Program Manual for EGCG Package, Peter Rice, The Sanger Centre, Hinxton Hall, Cambridge, CB10 1RQ, England) and the ExPASy World Wide Web Server for Molecular Biology (Geneva University Hospital and University of Geneva, Geneva, Switzerland).

The term “control sequence” as used herein refers to a DNA sequence, such as a functional promoter and any other relevant transcriptional element (e.g., an enhancer, a CCAAT box, a TATA box, and SPI site).

The term “operatively linked” as used herein refers to that an oligonucleotide is linked to a regulatory element which regulates gene expression, such as a promoter and an enhancer, in such a manner that a gene encoded by the oligonucleotide can be expressed in a host cell.

It is well known to those skilled in the art that the types and kinds of a control sequence vary depending on the host cell. Examples of control sequences well known to those skilled in the art include the CaMV35S promoter and the nopaline synthase promoter. A gene may be introduced into a plant using a known method. Examples of such known methods include a method mediated by *Agrobacterium* or a method of directly introducing a gene into a cell. An example of a method mediated by *Agrobacterium* is Nagel et al.’s method (Micribiol. Lett.,67,325(1990)). In this method, for example, an expression vector is first introduced into *Agrobacterium* using electroporation, and the transformed *Agrobacterium* is then introduced into a plant cell in accordance with a method described in Plant Molecular Biology Manual (S. B. Gelvin et al., Academic Press Publishers). Examples of known methods for directly introducing a gene into a cell include the electroporation method and the gene gun method.

A gene-introduced cell is selected for drug resistance, such as hygromycin resistance, and thereafter, is regenerated into a plant body using a commonly used method.

Generally, names and laboratory protocols as used herein are well known in this field. Recombinant techniques, polynucleotide synthesis, and microorganism culture and transformation (e.g., electroporation) are used within standard technologies. These techniques and protocols are described in various general publications in the field and in this specification (generally, see Sambrook et al., Molecular Cloning: A Laboratory Manual, 2nd Ed. (1989) Cold Spring Harbor Laboratory Press, Cold Spring Harbor, N.Y.). These publications are herein incorporated by reference.

The oligonucleotide of the present invention is representatively obtained by a method described herein. Alternatively, the oligonucleotide of the present invention may be obtained by chemical synthesis based on the sequence disclosed herein. For example, the oligonucleotide of the present invention may be synthesized using an oligonucleotide synthesizer (manufactured by Applied Bio Systems) in accordance with the specification provided by the manufacturer.

PCR amplification methods are well known in the field (PCR Technology: Principles and Applications for DNA Amplification, edited by HA Erlich, Freeman Press, New York, N.Y. (1992); PCR Protocols: A Guide to Methods and Applications, edited by Innis, Gelfland, Snisky, and White, Academic Press, San Diego, Calif. (1990): Mattila et al.

(1991) Nucleic Acids Res. 19: 4967; Eckert, K. A. and Kunkel, T. A. (1991) PCR Methods and Applications 1: 17; PCR, McPherson, Quirkes, and Taylor, IRL Press, Oxford). These publications are herein incorporated by reference.

EXAMPLES

Hereinafter, the present invention will be described by way of examples. The present invention is illustrated by the examples described below and is not limited to the examples.

Example 1

Activation of Tos17 by Culture and Characterization of a Resultant Mutant

A fully mature seed of Nipponbare, which is a variant of a japonica variety, was used as a starting material to conduct callus initiation culture and cell suspension culture as described above (Hirochika et al., 1996, supra). Tos17 was activated in accordance with Otsuki's method (1990) (Rice protoplast culture, Agriculture, Forestry and Fisheries Technical Information Society). Briefly, a fully mature rice seed was cultured in MS medium containing 2,4-dichlorophenoxyacetic acid (2,4-D) (Otsuki (1990), supra) (25° C., one month) for induction into callus. The resultant callus was cultured in N6 liquid medium including 2,4-D (Otsuki (1990), supra) for 5 months and was then transferred to regeneration medium (Otsuki (1990), supra). As a result, a regenerated rice (first generation (R1) plant) was obtained. About 30 R1 seeds were harvested for each of the resultant R1 rice individuals, and were planted in pots including soil or MES buffered agar medium (5 mM MES, pH5.7; 0.5% agarose) to obtain second generation (R2) plants which were then subjected to morphological analysis. A week after germination, the phenotype of each plant in the R2 group was carefully examined. As a result, it was found that about ⅓ of the R2 group of a strain, LRD1, had a defect in growth of the lateral roots. This suggests that the defect of the LRD1 strain in the growth of the lateral roots is caused by a recessive mutation of a single gene locus.

Example 2

Analysis of a Gene Disrupted by Tos17

In order to demonstrate that the defect of the LRD1 strain obtained in Example 1 in the growth of the lateral roots is caused by the recessive mutation of a single gene locus, sites flanking a target site (Ts) of the LRD1 strain into which Tos17 has been inserted by transposition were first amplified.

1. Amplification of Sequences Flanking the Site into which Tos17 is Newly Transposed DNA was prepared from R2 rice (LRD1 strain) obtained in Example 1 using a CTAB method (Murray and Thompson, 1980, Nucleic Acids Res., 8, 4321–4325). A Tos17 target site sequence was amplified by inverse PCR using total DNA as described above (Hirochika et al., 1996, supra; Sugimoto et al., 1994, Plant J., 5, 863–871).

Briefly, about 1 μg of total DNA from a regenerated plant possessing the new Tos17 target site was initially digested with XhoI/SalI. The digested DNA was purified by phenol/chloroform extraction and then ethanol precipitation, followed by ligation using T4 DNA ligase in a total volume of 400 μl at 12° C. overnight. Salts and ATP were removed from the ligation mixture using Ultra Free G3-LGC centrifugation unit (Millipore). One half of the ligated DNA was used as a template in PCR. An amplification reaction was conducted by two-stage PCR using the following two sets of primers. The first stage: Tos17 LTR1, TTGGATCTTGTATCTTGTATATAC and Tos17 LTR3, CCAATGGACTGGACATCCGATGGG. The second stage: Tos17 LTR-2, GCTAATACTATTGTTAGGTTGCAA and Tos17 LTR-4, CTGGACATGGGCCAACTATACAGT. A target site of a normal plant into which Tos17 was not inserted was not subjected to tissue culture, and was amplified using a primer TGAGTTCCCCTTGAGTCAGC and GTAGGACACTGGACAGTTGC. Thereafter, each of the inverse PCR products was cloned into the pBluescript vector (Stratagene), followed by sequencing using a sequencer (ABI, Model 377).

As a result of the sequencing of the flanking sequences of Tos17 in the LRD1 strain, nine target sites (Ts) (Ts1 to Ts9) for Tos17 insertion were newly found.

2. Linkage Analysis of the Phenotype of a Mutant and the Disruption of Ts9 Gene Locus An R2 group of the LRD1 strain in which growth of the lateral roots was inhibited was subjected to simultaneous separation analysis with Southern blotting using a Ts9 flanking sequence as a probe. Further, an R3 plant group which had been obtained by self-pollination of an R2 plant having a hetero type Ts9 flanking region (including a Tos17-inserted gene and a normal gene) was subjected to linkage analysis using a polymerase chain reaction kit (LA-PCR, TaKaRa Biomedicals). The following two primers flanking Ts9 (a target site into which Tos17 was newly transposed) were designed: a forward primer: GCAGCTATTACTGTCCTGTC and a reverse primer: CAAGTTAGGAGCGTCATGGA. One cycle of the amplification reaction was the following. Initiation degeneration: 96° C., 1 minute. Degeneration: 98° C., 20 seconds (30 cycles). Annealing: 57° C., 3 minutes. Elongation: 72° C., 5 minutes. By LA-PCR, an amplified product of 770 bp was obtained for a wild-type plant; an amplified product of 5.1 kbp was obtained for a mutant plant having a defect in growth of the lateral roots; and both of the amplified products were obtained for the hetero type plant. These were confirmed for about 100 plants in the R2 and R3 groups, and were closely linked to the phenotype having inhibited growth of lateral roots. Thus, it was confirmed that the defect of the LRD1 strain in the growth of lateral roots is caused by the recessive mutation of the single gene locus Ts9.

3. Construction of a cDNA Library and a Genomic Library and Characterization of Ts9

A wild type rice was grown in soil for four weeks, in which growth of the lateral roots was not inhibited. A root of the wild type rice was used to prepare RNA as follows. Initially, total RNA was extracted from a root using ISOGEN solution (Nippon gene). Poly(A) mRNA was obtained from the total RNA using an oligo (dt) cellulose column included in a mRNA purification kit (Stratagene). The resultant poly(A) mRNA was used to synthesize cDNA using a commonly used method to construct a cDNA library in λZAP-II vector (Stratagene). The cDNA library from the root had an infection ability of $5\times10^5$ plaques. A pBluescript plasmid having a positive cDNA insert was in vivo excised in *Escherichia coli* XL1-Blue MRF2 strain.

A genomic library was previously prepared by the inventors. The preparation method is briefly described below. Genomic DNA was partially digested with Sau3AI, and the resultant genome fragments were inserted into the EMBL3 vector (Frischauf et al., 1983, J. Mol. Biol., 170, 827–842).

These libraries were screened using an inverse PCR product of Ts9 as a probe in accordance with the method described in Molecular Cloning, A Laboratory Manual (Sambrook et al., 1989).

Clones having strong signals, which were obtained from the cDNA library and the genomic library, were further screened by PCR using a pair of primers specific to a Ts9 flanking sequence (Ts9F GGAACAGACAAAGAGC-GAAC, and Ts9R TTGCTGTCATGGCTGCTCCT) and agarose electrophoresis.

Four cDNA clones exhibiting strong hybridization signals were obtained from the cDNA library.

Out of four clones, the longest cDNA having a size of about 2 kb was sequenced in opposite directions using a 377 sequencer (Perkin Elmer). Further, the cDNA was subjected to homology analysis using open reading frame (ORF), and BLAST (Altshul et al., 1997, Nucleic Acids Res., 25, 3389–3402), and to hydrophobicity analysis using Mac Vector 6.0 program (Teijin system technology).

According to the sequencing analysis, it was found that the longest cDNA clone had a length of 2093 bp (SEQ ID NO. 1), and had four different polyadenylation sites (positions 1954, 1978, 2011 and 2093) at its 3' end. According to the analysis of mRNA using the Mac Vector 6.0 package, the longest 1215-bp open reading frame was identified, which encoded a protein consisting of 405 amino acids (SEQ ID NO. 2). This protein included a RING finger portion which is present in other proteins, such as G1 of *Drosophila*. This protein is designated as OsRing1. The 2093 bp sequence is shown in FIG. 1. A representative RING finger portion is present between nucleotide 1304 to 1426 of the sequence shown in FIG. 1, which consists of seven cysteine residues and one histidine residue. These residues are believed to be collectively involved in ionic bonding of two $Zn^{30}$ ions. It is known that the distance between a cysteine residue and a histidine residue is highly conserved in RING finger portions present in other proteins (Freemont et al., 1991, Cell, 64, 483–484). A cysteine-rich region of OsRing1 substantially matches a pattern of a representative RING finger portion, except that the fourth cysteine is replaced with a histidine residue. This character was found in the G1 gene of *Drosophila melanogaster* which is involved in embryonic development (Bouchard and Cote, 1993, Gene, 125, 205–209), and the ATL2 gene of *Arabidopsis thaliana* (Martinez-Garia, 1996, Mol. Gen. Genet, 252, 587–598).

Another character of the OsRing1 protein is that nonpolar residues are dominant (41.23% of the entirety) and there are four hydrophobic domains of 24, 16, 30 and 36 residues around the center (amino acid 85 to 108, amino acid 119 to 134, amino acid 196 to 225, and amino acid 237 to 272). Only 12 weakly-hydrophilic residues are present between the third and fourth hydrophobic domains. A domain including the third and fourth hydrophobic domains is considered to be the largest hydrophobic domain. In view of these characters, the inventors believe that the OsRing1 gene encodes a membrane-bound protein.

The structure of some positive genomic clones obtained from the genomic library was analyzed using restriction enzyme digestion, and polymerase chain reaction using the following pair of primers specific to terminal sequences of EMBL3 vector (LA-PCR, TaKaRa Biomedicals). EMBL3 (forward direction): ATGGTGTCCGACTTATGCCC, and EMBL3 (reverse direction): CTCGTCCGAGAATAAC-GAGT. The sequencing was conducted using two primers specific to the above-described full-length cDNA terminal sequences (forward: GAGAGCTACCTCGAATCGAA, and reverse direction: GCTCAACTCAGGTGATCATC). Specifically, a genomic clone containing a 14 kb insertion fragment was digested with HindIII and SalI to generate 5.3-kb fragments which were in turn subjected to LA-PCR using the above-described primers specific to the full-length cDNA sequence. It was confirmed that the fragments included a full-length open reading frame. It was found that the OsRing1 gene had five introns, and Tos17 was inserted at the third intron.

Example 3

Expression Analysis of the OsRing1 Gene

Expression inhibition of the OsRing1 gene caused by Tos17 insertion, which is observed in the mutant having a defect in growth of the lateral roots, was analyzed. To this end, RNA was extracted from mutant (homo) and wild type rice plants, followed by northern analysis, to study its expression characteristics.

The seeds of these lines were germinated in water for seven days, followed by cultivation in soil for 2, 4 and 6 weeks. Total RNA was extracted from roots and leaves from each of the plants, and stems and flower organs of each of the matured plants, and the callus using ISOGEN RNA extraction solution (Nippongene). mRNA was purified using an oligo dt-30 column (Nippongene). The mRNA was separated using 1.5% agarose gel containing 5% (v/v) formaldehyde solution. Further, DNA was extracted from the leaves of the plants using a CATB method (Rogers and Bendich, 1994), followed by digestion with XbaI. About 2 μg of poly(A) RNA and about 1 μg of DNA were subjected to electrophoresis. Prehybridization and hybridization were conducted in a solution containing 0.5 M of $NaH_2PO_4$—$Na_2HPO_4$ (pH 7.2), 7% SDS, 200 μg of calf thymus DNA at 68° C. for 3 and 12 hours, respectively, using a Ts9 inverse PCR product as a probe in accordance with the method described in Sambrook et al., 1989 (supra). After hybridization, a filter was washed twice in 2×SSC solution containing 0.5% SDS at 55° C. for a total of one hour.

As a result of the northern analysis (not shown), strong expression of the OsRing1 gene was detected in roots of the from two-week old to matured wild type rices which have lateral roots. The OsRing1 gene was also expressed in the flower organs at a relatively high level. However, the OsRing1 gene was expression at a low level in the callus culture, and at a significantly low level in the leaves from all stages from the seedling to the matured plant.

Formation of lateral roots can be simulated by cutting all roots of the four-week old plant grown in soil, or using a plant grown in a pot which has no lateral root. In the plant whose roots were removed, a primary root without lateral roots appeared at a base of a shoot one week after transplantation, and a number of lateral roots were produced from the primary root after 2 to 3 weeks. Northern analysis was conducted. It was found that the OsRing1 gene was very strongly expressed in the root having a number of lateral roots but very weakly expressed in the primary root. These results indicate that the expression of the OsRing1 gene has close linkage with the formation or growth of the lateral root.

In the mutant having the inhibited growth of lateral roots, the OsRing1 is not expressed due to the Tos17 insertion. The mechanism of such a phenomenon was studied by synthesizing a sequence upstream of the Tos17 insertion site using PCR. Northern blotting analysis was conducted using the sequence as a probe. As a result, in the mutant having inhibited growth of lateral roots, 2.1 kb RNA which is expected from the OsRing1 sequence was not detected, but 0.9 kb RNA was detected (not shown). The size of 0.9 kb corresponds to a sequence from the 5' end of cDNA to the Tos17 insertion site of the OsRing1 mutant. This indicates that the OsRing1 expression was interrupted due to the Tos17 insertion, and partial OsRing1 mRNA which does not have a RING finger sequence was accumulated in the mutant. A similar example of the removal of gene expression due to Tos17 has been reported in stripe mutation due to Tos17 insertion (privately communicated by M Yamasaki).

Example 4

Complementation Test Using OsRing1 Gene Introduction

1. Construction of Complementary Vector and Transformation of the OsRing1 Mutant Using *Agrobacterium tumefaciens*

A 5.3 kb SalI/HindIII fragment including an open reading frame of the full-length OsRing1 gene was incorporated into the pIG121-Hm vector by linking downstream of the CaMV35S promoter (Akama et al., 1992, Plant Cell Rep., 12, 7–11) (FIG. 2). The resultant vector is designated as pIG121-Hm-RF. *Agrobacterium tumefaciens* EHA101 strain was transformed with the recombinant vector by electroporation, followed by screening using 50 mg/l of kanamycin and hygromycin. The resultant *Agrobacterium* strain was cryopreserved until future use.

The seed of the OsRing1 mutant was sterilized with 1% sodium hypochlorite, and washed with sterilized distilled water five times. The seed was placed on N6 medium containing 3% sucrose, 0.3 g/l casein hydrolysate, 2.8 g/l proline, and 2.0 mg/l 2,4-D, which was solidified with 5.0 g/l gellan gum (Chu et al., 1975, Sci. Sinica, 18, 659–668). The pH of the medium had been adjusted to pH 5.8 before being autoclaved. The seed was grown in the dark at 28° C. for two weeks, thereby obtaining a small callus having a size of about 2 mm. The small callus was transferred to a callus inducing medium and cultured in the light for four days. The resultant callus was subjected to *Agrobacterium* infection.

The above-described lyophilized *Agrobacterium* was cultured in the dark at 22° C. for 3 days in AB medium containing 50 mg/l kanamycin and 50 mg/l hygromycin, which was adjusted to pH 7.2 and solidified with 15 g/l agar (Chilton et al., 1974, Proc. Natl. Acad. Sci. USA, 71, 3672–3676). *Agrobacterium* bacteria were collected and suspended in liquid AAM medium (Hiei et al., 1994, Plant J., 6, 271–282) containing 20 μg of acetosyringone (Hiei et al., 1994). The resultant suspension was co-incubated with the above-described induced callus in the dark at 22° C. for seven days so that the callus was infected with *Agrobacterium*. The resultant callus was washed five times with liquid callus inducing medium containing 500 mg/l of carbenicillin, followed by drying on a sterilized Whatman No. 1 filter paper. The callus was cultured for three weeks on a callus inducing medium containing 50 mg/l hygromycin to select a hygromycin-resistance callus, which was then transferred to regeneration medium containing MS basal medium (pH 5.8) (Murashige and Skoog, 1962, Physiol. Plant., 15, 473–497) containing 30 g/l sucrose, 30 g/l sorbitol, 2 g/l casein hydrolysate, 2 g/l kinetin, 500 mg/l carbenicillin, 50 mg/l hygromycin and 5/l gel gum.

Figure 3:
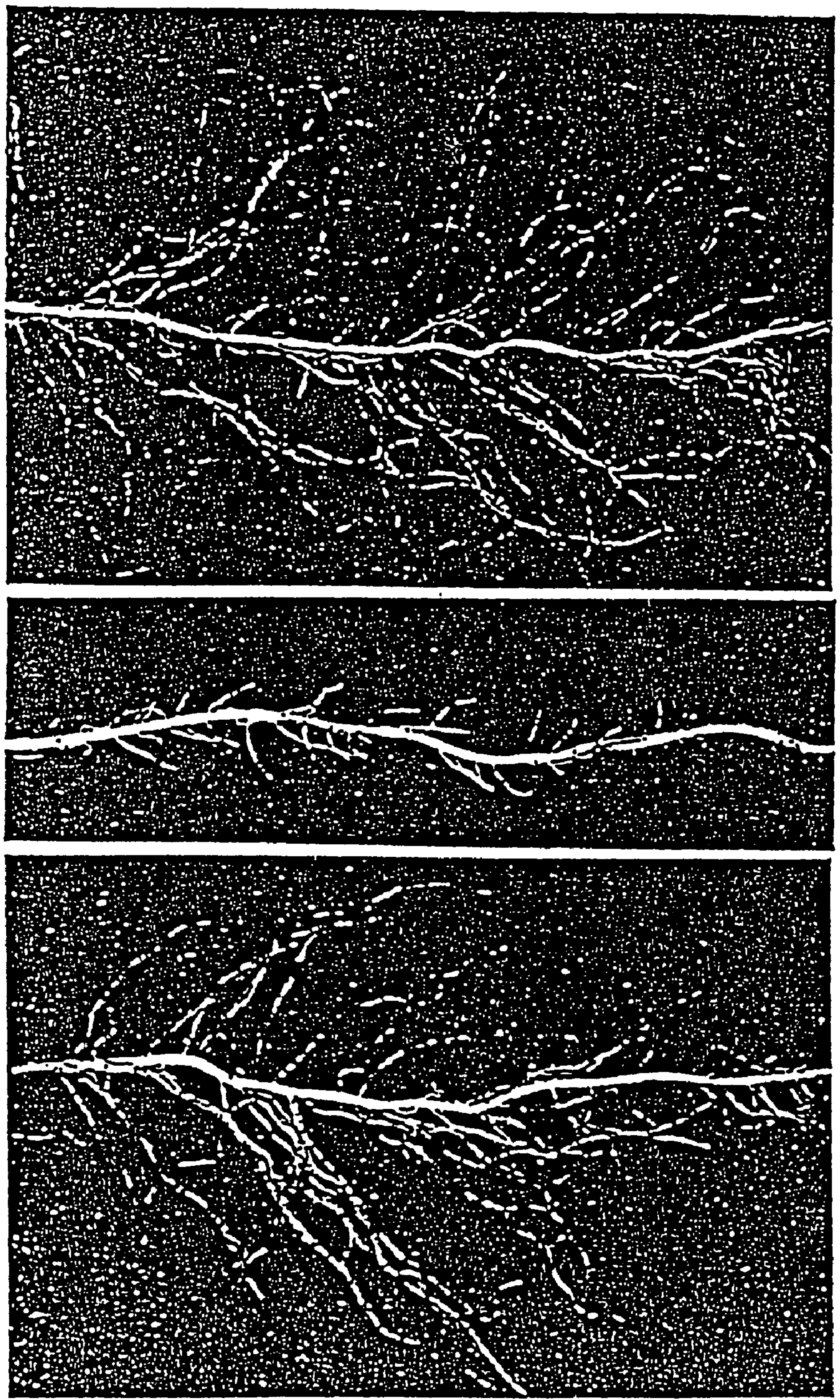
FIG. 3 is a photograph showing the growth of lateral roots in a Tos17 insertion mutant and a transformant obtained by introducing the oligonucleotide of the present invention. From the left, shown are a control (wild type rice root), the growth of lateral roots in the Tos17 insertion mutant, and the growth of lateral roots in the transformant obtained by introducing the oligonucleotide of the present invention. As compared to the wild type (left), in the Tos17 insertion mutant (middle), the growth of lateral roots is significantly inhibited. In the transformant obtained by introducing the oligonucleotide of the present invention (right), the growth of lateral roots was recovered to the level of the wild type.

The transformant was easily regenerated in regeneration medium containing hygromycin without auxin or NAA, and transferred to soil. As shown in FIG. 3, the transformant exhibited normal growth of lateral roots. This result leads to the conclusion that mutation of the OsRing1 gene is responsible for the inhibition of the growth of lateral roots.

Example 5

Functional Analysis of the OsRing1 Gene

It has been reported that the growth of lateral roots is inhibited by ethylene (Jackson M. B., 1991, "Ethylene in root growth and development" in The Plant Hormone Ethylene, edited by A. K. Matto and J. C. Suttle, 159–181, CRC Press, Boca Raton, Fla. ISBN 0-8493-4566-9). Whether inhibited growth of lateral roots in a mutant is correlated with ethylene was studied.

Seeds of a mutant and a corresponding wild type progeny were sterilized with 1.0% sodium hypochlorite and thoroughly washed, followed by immersion under water at 25° C. for 24 hours. The seeds was placed horizontally on 5 mM MES (2-[N-Morpholino]ethanesuflonic acid, $C_6H_{13}NO_4S$, manufactured by Sigma) buffered agar medium (pH 5.8) in the dark at 25° C. for seven days for the purpose of morphological analysis in the presence or absence of $10^{-9}$ to $10^{-5}$ M auxin (manufactured by Sigma), $10^{-6}$, to $10^{-3}$ M ACC (1-aminocyclopropane-1-carboxylic acid; an ethylene synthesis precursor, manufactured by Sigma), or $10^{-10}$ to $10^{-7}$ M $AgNO_3$: an ethylene synthesis inhibitor (Smalle J. et al., 1997, "Ethylene can stimulate *Arabidopsis* hypocotyl elongation in the light", Proc. Natl. Acad. Sci. USA, 94: 2756–2761). Roots of these seeds were fixed with formalin-acetic acid-alcohol (FAA) fixation solution, cleared with a chloral hydrate solution (Yadegari, R. et al., 1994, "Cell differentiation and morphogenesis are uncoupled in *Arabidopsis* raspberry embryos", Plant Cell 6: 1713–1729), and observed using a differential interference microscope.

Figure 4:
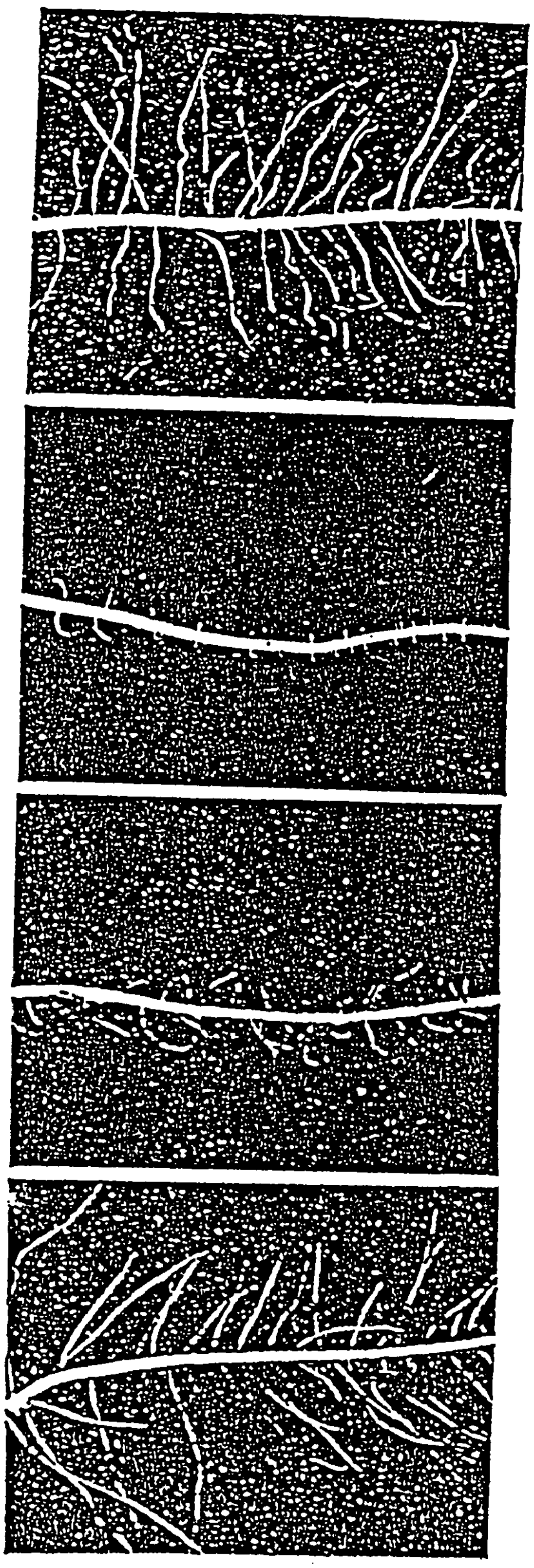
FIG. 4 is a diagram showing effects of the ethylene precursor ACC and the ethylene inhibitor $AgNO_3$ on the growth of lateral roots. From the left, shown are the growth of lateral roots of a wild type rice (untreated), a wild type rice (treated with $10^{-4}$ M ACC), a Tos17 insertion mutant (untreated), and a Tos17 insertion mutant (treated with $10^{-7}$ M $AgNO_3$). If a wild type is treated with ACC, the growth of lateral roots is inhibited. If a Tos17 insertion mutant is treated with $AgNO_3$, the growth of lateral roots was recovered to a normal level.

As a result, in a wild type rice which was placed in a germination medium containing ACC (0.5% agar (INA AGAR, Funakoshi)), growth of the lateral roots was significantly inhibited (FIG. 4). In contrast, in a mutant which was grown in germination medium containing 7 to 10 M $AgNO_{31}$ the growth of lateral roots was improved to the level of a wild type. This phenomenon suggests that in the mutant, the amount of ethylene production is increased in the roots.

Example 6

Measurement of the Amount of Ethylene Production

The amount of ethylene production in each organ of a wild type and a mutant was measured using gas chromatography.

A sprout which had been grown in the dark at 25° C. for seven days, was divided into coleoptile (above-ground part) and root, which were loaded into 50 mL tubes and sealed, followed by culture in the dark at 25° C. After 20 hours, 1 mL of gas was collected from each tube containing the sample using a syringe, and the amount of ethylene was measured by gas chromatography (GC-8AIF, manufactured Shimazu Corporation) under the following conditions.

(Measurement Conditions for Gas Chromatography)

Column: activated alumina, Column temperature: 60° C., Temperature of a sample furnace: 90° C., Detector: flame ionization detector (FID) (hydrogen flow rate: 60 KPa, air flow rate: 50 KPa), Carrier gas: nitrogen, Carrier gas flow rate: 60 KPa. In this case, the retention time of ethylene was 0.5 minutes.

Figure 5:
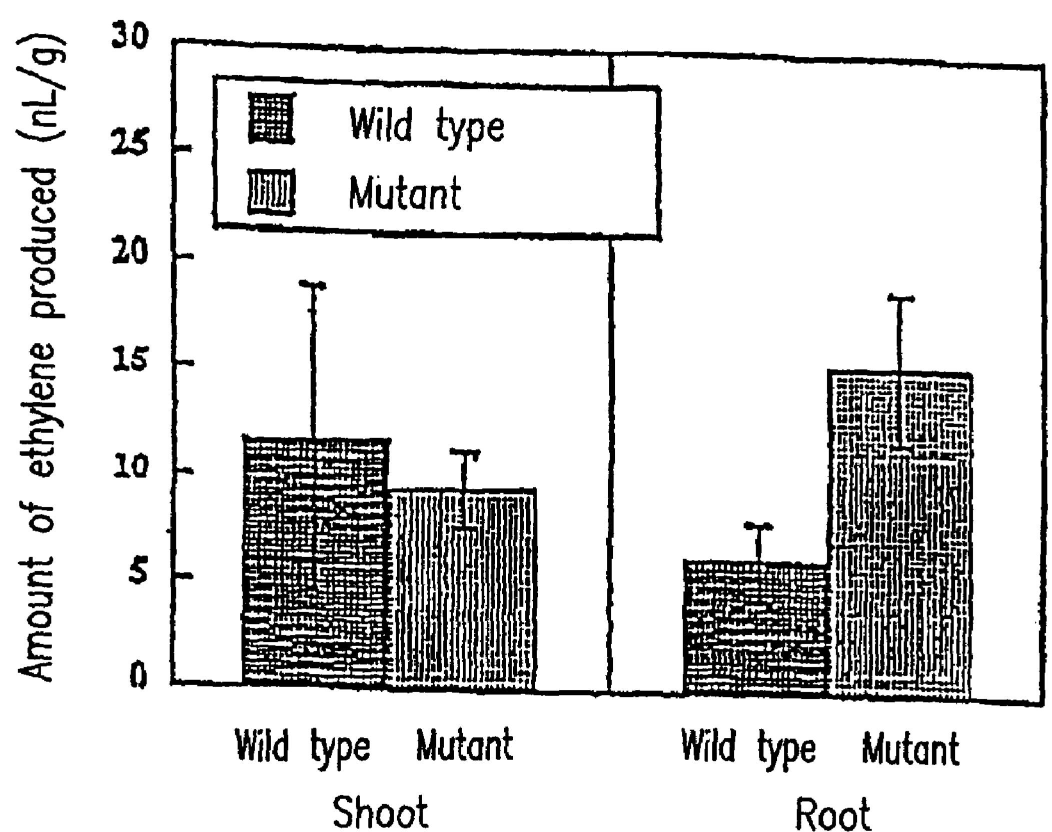
FIG. 5 is a diagram showing comparison between the amounts of ethylene produced in a wild type and a mutant.

The results are shown in FIG. 5. As shown in FIG. 5, the amount of ethylene produced was significantly increased in the mutant as compared to the wild type. This result shows that the OsRing1 gene is responsible for inhibition of ethylene synthesis in root.

The above-described Examples illustrate various aspects of the present invention, and preparation and utilization of the specific oligonucleotides of the present invention and are not intended to limit the scope of the present invention.

INDUSTRIAL APPLICABILITY

A novel oligonucleotide capable of controlling ethylene synthesis is provided, which may be useful in plant breeding. A plant is provided by introducing the oligonucleotide into the plant to control ethylene synthesis. The plant is given the following properties: acceleration of growth of lateral roots, submergence resistance, and improved ability to retain the quality of fruit and flower.

The invention claimed is:

1. An oligonucleotide encoding a plant protein capable of controlling ethylene synthesis, comprising an amino acid sequence from position 1 (Met) to 405 (Gln) of SEQ ID NO: 2.

2. The oligonucleotide according to claim 1, wherein the oligonucleotide is from rice.

3. The oligonucleotide according to claim 1, wherein the oligonucleotide is by SEQ ID NO. 1.

4. A vector comprising the oligonucleotide of claim 1 operatively linked to a control sequence.

5. A method for inhibiting the levels of ethylene synthesis in rice roots, comprising the step of introducing an oligonucleotide according to claim 1 into a rice plant, wherein the protein is expressed and the levels of ethylene are inhibited.

* * * * *

```
                              SEQUENCE LISTING

<160> NUMBER OF SEQ ID NOS: 2

<210> SEQ ID NO 1
<211> LENGTH: 2105
<212> TYPE: DNA
<213> ORGANISM: Oryza sativa
<220> FEATURE:
<221> NAME/KEY: CDS
<222> LOCATION: (313)..(1527)
<223> OTHER INFORMATION:

<400> SEQUENCE: 1

gcgtaagaaa aataaaagga gaaaaaggaa tagagaaatt ggggaagaga gctacctcga      60

atcgaagctg cgatctccac ctggtgaaat aggagaattg atgaattgct gagatttggt     120

gattagaggg acctttgctg ctgaggcatt gaggtacact aaaagcaagg gtgtgaaaaa     180

ggcaacttca attgaaaaca tctacatatc taggaatgtc ctgaaactaa tgtgtggagt     240

aaacttctag tttattgctg tccgtcctgt tgggccacag tgcgaaggtc aggcagtagt     300

catccattac tg atg ggg gac tct gga aat gcc agt cat cgt gat cac acg     351
              Met Gly Asp Ser Gly Asn Ala Ser His Arg Asp His Thr
              1               5                   10

atc gac ata ctg aga aat gat gca act ttc cca tca aca tct cat cag       399
Ile Asp Ile Leu Arg Asn Asp Ala Thr Phe Pro Ser Thr Ser His Gln
    15                  20                  25

gat aat cat aat aac ttg gat gag ttg cac caa act aga ggg cct cta       447
Asp Asn His Asn Asn Leu Asp Glu Leu His Gln Thr Arg Gly Pro Leu
30                  35                  40                  45

aat gat gtt cct cat gtc cca gaa agt tct gct agt gca act cct gca       495
Asn Asp Val Pro His Val Pro Glu Ser Ser Ala Ser Ala Thr Pro Ala
                50                  55                  60

tct atc tcc cga aac gct tct ttt gca aga aga gat caa gaa cac cgt       543
Ser Ile Ser Arg Asn Ala Ser Phe Ala Arg Arg Asp Gln Glu His Arg
            65                  70                  75

caa cca aat cct ttg aat tct ggc ttc tgg atc tca att gag ctt att       591
Gln Pro Asn Pro Leu Asn Ser Gly Phe Trp Ile Ser Ile Glu Leu Ile
        80                  85                  90

gta agt tta agc cag att ata gca gct att act gtc ctg tca gta tca       639
Val Ser Leu Ser Gln Ile Ile Ala Ala Ile Thr Val Leu Ser Val Ser
    95                  100                 105

agg aac gag cat cct cat gct cct ttg gct cag tgg ctt att ggt tat       687
Arg Asn Glu His Pro His Ala Pro Leu Ala Gln Trp Leu Ile Gly Tyr
110                 115                 120                 125

acg ata ggt tgt gtt gct act ctt cct cac ctt tat tgg cga ttt ctc       735
Thr Ile Gly Cys Val Ala Thr Leu Pro His Leu Tyr Trp Arg Phe Leu
                130                 135                 140

cac cgc aat cgg cag aac aca gag caa gaa tca aca aat cag gtt tca       783
His Arg Asn Arg Gln Asn Thr Glu Gln Glu Ser Thr Asn Gln Val Ser
            145                 150                 155

tct gaa agg gac gta tat gag cct aat tct tat gta gta gtt tcg tct       831
```

-continued

```
Ser Glu Arg Asp Val Tyr Glu Pro Asn Ser Tyr Val Val Val Ser Ser
        160                 165                 170

gct cat gga tca gaa gtt gtg gac agt ggt aat aat ggt gga gta gca      879
Ala His Gly Ser Glu Val Val Asp Ser Gly Asn Asn Gly Gly Val Ala
    175                 180                 185

agg att gca agt cca agg gtc tac gca ttg gtt gcg tgc ttc aaa ttg      927
Arg Ile Ala Ser Pro Arg Val Tyr Ala Leu Val Ala Cys Phe Lys Leu
190                 195                 200                 205

gct ctg gat tgt ttc ttt gct gtg tgg ttt gtt gtt ggg aat gtg tgg      975
Ala Leu Asp Cys Phe Phe Ala Val Trp Phe Val Val Gly Asn Val Trp
                210                 215                 220

ata ttc ggg ggc cgt act tct ctc cat gac gct cct aac ttg tac agg     1023
Ile Phe Gly Gly Arg Thr Ser Leu His Asp Ala Pro Asn Leu Tyr Arg
            225                 230                 235

ctg tgc ata gta ttc ctt gca ttc ggc ttc atc ggc tat gcc ctg cct     1071
Leu Cys Ile Val Phe Leu Ala Phe Gly Phe Ile Gly Tyr Ala Leu Pro
        240                 245                 250

ttc atc cta tgt aca atg ata tgc tgc tgc cta ccc tgc att atc tcc     1119
Phe Ile Leu Cys Thr Met Ile Cys Cys Cys Leu Pro Cys Ile Ile Ser
    255                 260                 265

atg atg ggc atc cac gag gat ttg gat ttt aac aga ggc gct act gca     1167
Met Met Gly Ile His Glu Asp Leu Asp Phe Asn Arg Gly Ala Thr Ala
270                 275                 280                 285

gaa gca atc gat gcc ttg gtg gca tac aag ttc caa tcg aaa aag ttt     1215
Glu Ala Ile Asp Ala Leu Val Ala Tyr Lys Phe Gln Ser Lys Lys Phe
                290                 295                 300

caa gat gga gaa gcg gga gaa gat aat ggt gga gta ttg gca gct gga     1263
Gln Asp Gly Glu Ala Gly Glu Asp Asn Gly Gly Val Leu Ala Ala Gly
            305                 310                 315

aca gac aaa gag cga act att tct gca gaa gac gct gta tgc tgc atc     1311
Thr Asp Lys Glu Arg Thr Ile Ser Ala Glu Asp Ala Val Cys Cys Ile
        320                 325                 330

tgc ttg tca aag ttc tca aac aac gaa gat cta cgg gag ctt ccc tgc     1359
Cys Leu Ser Lys Phe Ser Asn Asn Glu Asp Leu Arg Glu Leu Pro Cys
    335                 340                 345

aat cat gtt ttc cac ttg gaa tgc gtc gat aaa tgg ctc aag ata aac     1407
Asn His Val Phe His Leu Glu Cys Val Asp Lys Trp Leu Lys Ile Asn
350                 355                 360                 365

gca ctg tgc cct ctt tgc aag gct gac tta ggc ggc tcg acg aat gct     1455
Ala Leu Cys Pro Leu Cys Lys Ala Asp Leu Gly Gly Ser Thr Asn Ala
                370                 375                 380

ccg gac tcg agc tcc agg agc agc cat gac agc aac aac agc aga gtc     1503
Pro Asp Ser Ser Ser Arg Ser Ser His Asp Ser Asn Asn Ser Arg Val
            385                 390                 395

agg aac gac gtc gag tca caa cag tagctgctct catgcccttt cccatgagca    1557
Arg Asn Asp Val Glu Ser Gln Gln
        400                 405

tggggatgga acacattctt gacaatctac aaattggcat gcaacttctc aagtcccttt   1617

ttttttcaga cagacttgaa tagagcattt gcctacactg ctctctggtg ttaacccaga   1677

aactcctatg aggctgaggc tatggctatg agttgctgcc tgcagtttgt tctgaactga   1737

agttgcctgt aaggctgtaa cagattatag atggtgttgg aatagttatc atgatgatca   1797

cctgagttga gcatattagg ttgttgaggt taaccttcaa ccggggaggt tcaatgtaat   1857

tatctccttg tttaggaaaa aatcccctcc cctttgtatt tgctcccttg tatagaaaac   1917

aaccatttcc attgtatatc agatcaattt tgcctgcatt ttgtaaattc agttagtagg   1977

cagagatttc ccagcaatca tcaagcggtt gagcaagtac agattagcag ttgagtttat   2037
```

-continued

```
tttactgtaa tgcaacaatt atagatgata ttaccatgaa ataatcattt gagcccaaaa   2097

aaaaaaaa                                                            2105


<210> SEQ ID NO 2
<211> LENGTH: 405
<212> TYPE: PRT
<213> ORGANISM: Oryza sativa var. nipponbare

<400> SEQUENCE: 2

Met Gly Asp Ser Gly Asn Ala Ser His Arg Asp His Thr Ile Asp Ile
  1               5                  10                  15

Leu Arg Asn Asp Ala Thr Phe Pro Ser Thr Ser His Gln Asp Asn His
             20                  25                  30

Asn Asn Leu Asp Glu Leu His Gln Thr Arg Gly Pro Leu Asn Asp Val
         35                  40                  45

Pro His Val Pro Glu Ser Ser Ala Ser Ala Thr Pro Ala Ser Ile Ser
     50                  55                  60

Arg Asn Ala Ser Phe Ala Arg Arg Asp Gln Glu His Arg Gln Pro Asn
 65                  70                  75                  80

Pro Leu Asn Ser Gly Phe Trp Ile Ser Ile Glu Leu Ile Val Ser Leu
                 85                  90                  95

Ser Gln Ile Ile Ala Ala Ile Thr Val Leu Ser Val Ser Arg Asn Glu
            100                 105                 110

His Pro His Ala Pro Leu Ala Gln Trp Leu Ile Gly Tyr Thr Ile Gly
        115                 120                 125

Cys Val Ala Thr Leu Pro His Leu Tyr Trp Arg Phe Leu His Arg Asn
    130                 135                 140

Arg Gln Asn Thr Glu Gln Glu Ser Thr Asn Gln Val Ser Ser Glu Arg
145                 150                 155                 160

Asp Val Tyr Glu Pro Asn Ser Tyr Val Val Val Ser Ser Ala His Gly
                165                 170                 175

Ser Glu Val Val Asp Ser Gly Asn Asn Gly Gly Val Ala Arg Ile Ala
            180                 185                 190

Ser Pro Arg Val Tyr Ala Leu Val Ala Cys Phe Lys Leu Ala Leu Asp
        195                 200                 205

Cys Phe Phe Ala Val Trp Phe Val Val Gly Asn Val Trp Ile Phe Gly
    210                 215                 220

Gly Arg Thr Ser Leu His Asp Ala Pro Asn Leu Tyr Arg Leu Cys Ile
225                 230                 235                 240

Val Phe Leu Ala Phe Gly Phe Ile Gly Tyr Ala Leu Pro Phe Ile Leu
                245                 250                 255

Cys Thr Met Ile Cys Cys Cys Leu Pro Cys Ile Ile Ser Met Met Gly
            260                 265                 270

Ile His Glu Asp Leu Asp Phe Asn Arg Gly Ala Thr Ala Glu Ala Ile
        275                 280                 285

Asp Ala Leu Val Ala Tyr Lys Phe Gln Ser Lys Lys Phe Gln Asp Gly
    290                 295                 300

Glu Ala Gly Glu Asp Asn Gly Gly Val Leu Ala Ala Gly Thr Asp Lys
305                 310                 315                 320

Glu Arg Thr Ile Ser Ala Glu Asp Ala Val Cys Cys Ile Cys Leu Ser
                325                 330                 335

Lys Phe Ser Asn Asn Glu Asp Leu Arg Glu Leu Pro Cys Asn His Val
            340                 345                 350

Phe His Leu Glu Cys Val Asp Lys Trp Leu Lys Ile Asn Ala Leu Cys
```

-continued

```
        355                 360                 365

Pro Leu Cys Lys Ala Asp Leu Gly Gly Ser Thr Asn Ala Pro Asp Ser
    370                 375                 380

Ser Ser Arg Ser Ser His Asp Ser Asn Asn Ser Arg Val Arg Asn Asp
385                 390                 395                 400

Val Glu Ser Gln Gln
                405
```